United States Patent
Lee et al.

(10) Patent No.: US 11,578,018 B1
(45) Date of Patent: Feb. 14, 2023

(54) INTEGRATED PROCESS FOR PRODUCING BTX AND HYDROGEN FROM SHALE GAS WITH FEEDING OF CARBON DIOXIDE

(71) Applicant: SOGANG UNIVERSITY RESEARCH & BUSINESS DEVELOPMENT FOUNDATION, Seoul (KR)

(72) Inventors: Jinwon Lee, Seoul (KR); Wonho Jung, Seoul (KR); Do Heui Kim, Seoul (KR); Kyoung-Su Ha, Seoul (KR); Woojae Kim, Seoul (KR); Seulah Lee, Seoul (KR); Hyeona Kim, Seoul (KR)

(73) Assignee: SOGANG UNIVERSITY RESEARCH & BUSINESS DEVELOPMENT FOUNDATION

( * ) Notice: Subject to any disclaimer, the term of this patent is extended or adjusted under 35 U.S.C. 154(b) by 0 days.

(21) Appl. No.: 17/586,358

(22) Filed: Jan. 27, 2022

(30) Foreign Application Priority Data

Nov. 3, 2021 (KR) ........................ 10-2021-0149491

(51) Int. Cl.
| | |
|---|---|
| *C07C 2/84* | (2006.01) |
| *C07C 7/144* | (2006.01) |
| *C07C 7/04* | (2006.01) |
| *C01B 3/44* | (2006.01) |
| *C01B 3/40* | (2006.01) |

(52) U.S. Cl.
CPC ................ *C07C 2/84* (2013.01); *C01B 3/40* (2013.01); *C01B 3/44* (2013.01); *C07C 7/04* (2013.01); *C07C 7/144* (2013.01); *C01B 2203/0238* (2013.01); *C01B 2203/1082* (2013.01); *C01B 2203/1241* (2013.01); *C01B 2203/14* (2013.01); *C07C 2523/28* (2013.01); *C07C 2529/48* (2013.01)

(58) Field of Classification Search
CPC .. C07C 2/84; C07C 7/04; C07C 7/144; C07C 2523/28; C07C 2529/48; C01B 3/40; C01B 3/44; C01B 2203/0238; C01B 2203/1082; C01B 2203/1241; C01B 2203/14
See application file for complete search history.

(56) References Cited

U.S. PATENT DOCUMENTS 7,355,088 B2  4/2008  Mamedov et al.

FOREIGN PATENT DOCUMENTS

KR  20170000055 A  1/2017

OTHER PUBLICATIONS

W. Li, et al., "Economic, Exergy, Environmental (3E) Analysis of Methanol Production from Shale Gas", Chem. Eng. Trans., 76, 655-660, (2019).

A.P. Ortiz-Espinoza et al., "Shale Gas as an Option for the Production of Chemicals and Challenges for Process Intensification", Process Intensification and Integration for Sustainable Design, 1st ed., WILEY-VCH Gmby, pp. 1-14, 2021.

(Continued)

*Primary Examiner* — Thuan D Dang
(74) *Attorney, Agent, or Firm* — Harness, Dickey & Pierce, P.L.C.

(57) ABSTRACT

An integrated process is provided for producing benzene, toluene, and/or xylene and hydrogen from shale gas under the feeding of carbon dioxide. The integrated process for producing an aromatic compound and hydrogen can efficiently and continuously produce high value-added aromatic compounds and hydrogen without the need to separate methane from shale gas through cryogenic distillation.

18 Claims, 4 Drawing Sheets

(56) References Cited

OTHER PUBLICATIONS

S.I. Perez-Uresti et al., "Techno-Economic Assessment of Benzene Production from Shale Gas", Processes, 5, 33, pp. 1-10, (2017).
J.J. Spivey et al., "Catalystic aromization of methane", Chem. Soc. Rev., 43, pp. 792-803 (2014).
Q. Li et al., "Investigation on the light alkanes aromatization over Zn and Ga modified HZSM-5 catalysts in the presence of methane", Fuel 219, pp. 331-339, (2018).
Y. Xiang et al., "Progress and prospects in catalytic ethane aromatization", Catalysis Science & Technology, 9, pp. 1500-1516, (2018).
E. Gomez et al., "Tandem Reactions of CO2 Reduction and Ethane Aromatization" to be published in Journal of the American Chemical Society, 42 pgs., Nov. 2019.

INTEGRATED PROCESS FOR PRODUCING BTX AND HYDROGEN FROM SHALE GAS WITH FEEDING OF CARBON DIOXIDE

NATIONAL SUPPORT RESEARCH AND DEVELOPMENT

This study was supported by the National Research Foundation of Korea (NRF) grant funded by the Korean government (MSIP) (No. 2015M3D3A1A01064929).

CROSS-REFERENCE TO RELATED APPLICATION

This application claims priority to Korean Patent Application No. 10-2021-0149491, filed on Nov. 3, 2021, and all the benefits accruing therefrom under 35 U.S.C. § 119, the contents of which in their entirety are herein incorporated by reference.

BACKGROUND

Technical Field

The present invention relates to an integrated process for producing benzene, toluene, and/or xylene (BTX) and hydrogen from shale gas under the feeding of carbon dioxide. Specifically, the present invention relates to a process for continuously producing BTX and hydrogen in which a process for producing BTX from shale gas under the feeding of carbon dioxide and a water-gas shift process for producing hydrogen by reacting carbon monoxide generated as a by-product in the former process with water are integrated.

Related Art

Research to utilize shale gas as an alternative to a sustainable energy source has been continuously conducted. In the United States, the production of shale gas per annum was increased from about 36.5 billion cubic meters to 4.3 trillion cubic meters from 2007 to 2015; it is estimated to increase annually by 13.5% until 2030.

As a method of utilizing shale gas, a technology has been proposed in which methane as a main component is separated from shale gas through cryogenic distillation, and it is then converted to various compounds. For example, W. Li, et al., Chem. Eng. Trans., 76, 655 (2019); "Shale Gas as an Option for the Production of Chemicals and Challenges for Process Intensification," Process Intensification and Integration for Sustainable Design, 1$^{st}$ ed., WILEY-VCH GmbH, 2021, and the like propose a process for separating methane and intermediate hydrocarbons from shale gas through cryogenic distillation and producing methanol from methane via synthesis gas. However, cryogenic distillation has disadvantages such as high latent heat of methane and ethane, the use of refrigerants for low-temperature operations, and high operating pressures.

S. I. Perez-Uresti, et al., Processes, 5, 33 (2017) proposes a process for separating methane and intermediate hydrocarbons from shale gas through cryogenic distillation and producing benzene from methane. However, this process still has the disadvantage of cryogenic distillation. In addition, a process for producing benzene from methane in the presence of an oxidizing agent such as carbon dioxide has been proposed (see J. J. Spivey, et al., Chem. Soc. Rev., 43, 792 (2014)); however, this process still has the disadvantage of cryogenic distillation.

Meanwhile, when aromatic compounds are produced from light alkanes in the presence of a zeolite catalyst, coke generated by pyrolyzing thermally less stable light alkanes rapidly deactivates the catalyst (see Q. Li, et al., Fuel, 219 331 (2018)). In addition, minimizing coke formation during the catalytic reactions is particularly challenging since both the aromatization of light alkanes and the coke formation are thermodynamically favored at high temperatures and low pressures (see Y. Xiang, et al., Catalysis Science & Technology, 8, 1500 (2018)).

Thus, it is required to develop a process capable of efficiently producing high value-added products from shale gas while the disadvantages of the prior art are mitigated.

Accordingly, an object of the present invention is to provide an integrated process for continuously producing BTX and hydrogen from shale gas under the feeding of carbon dioxide.

SUMMARY

According to an embodiment of the present invention, there is provided an integrated process for producing an aromatic compound and hydrogen, which comprises (1) coaromatizing a hydrocarbon feed comprising at least one of methane, ethane, and propane in the presence of a catalyst under the feeding of carbon dioxide to prepare an aromatic compound-containing product comprising at least one of benzene, toluene, and xylene, methane, hydrogen, and carbon monoxide; (2) separating from the aromatic compound-containing product (a) hydrogen, (b) the at least one of benzene, toluene, and xylene, and (c) a first methane-containing mixture comprising methane and carbon monoxide, respectively; and (3) subjecting the first methane-containing mixture to a water-gas shift to prepare a second methane-containing mixture comprising methane, hydrogen, and carbon dioxide.

Advantageous Effects of the Invention

The integrated process for producing an aromatic compound and hydrogen according to an embodiment of the present invention can efficiently and continuously produce high value-added aromatic compounds and hydrogen without the need to separate methane from shale gas through, e.g., cryogenic distillation.

In addition, this process can increase the regeneration efficiency of the catalyst and reduce the regeneration cost while extending the operating time of the reactor for producing aromatic compounds from shale gas.

DETAILED DESCRIPTION

Figure 1:
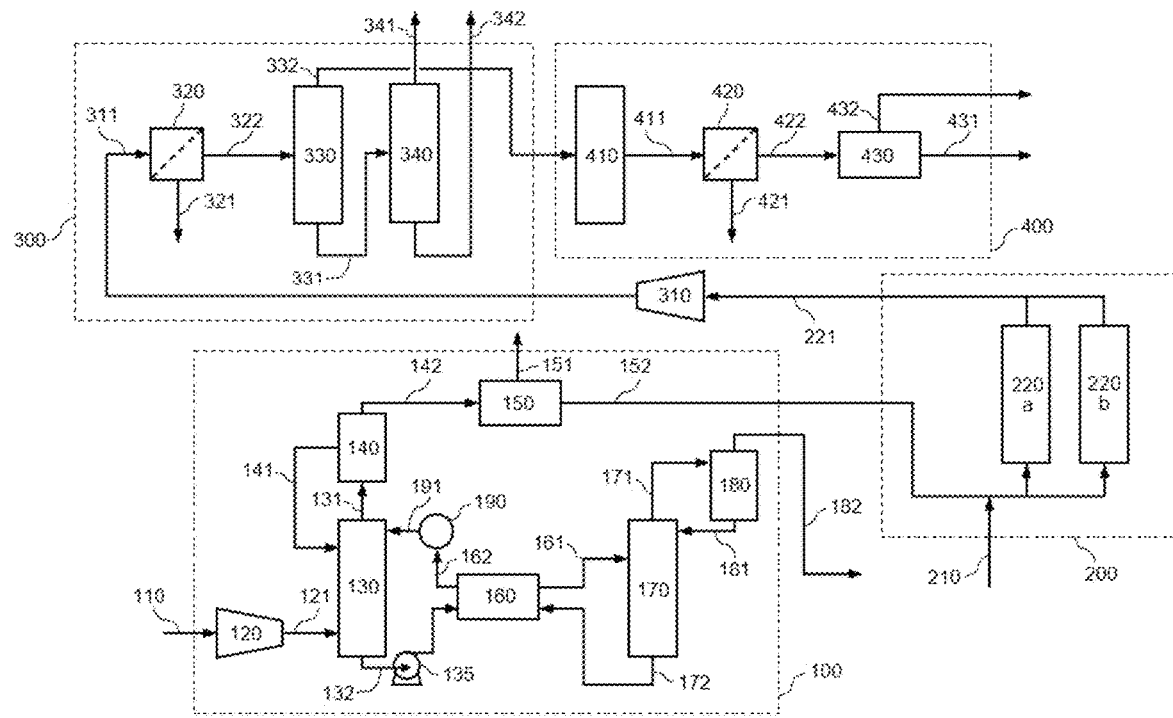
FIG. 1 is a flow diagram of an integrated process for producing an aromatic compound and hydrogen according to an embodiment of the present invention.

Hereinafter, the present invention will be described in more detail.

Throughout the present specification, when a part is referred to as "comprising" an element, it is understood that other elements may be comprised, rather than other elements are excluded, unless specifically stated otherwise.

In the present specification, a singular expression is interpreted to cover a singular or plural number that is interpreted in context unless otherwise specified.

In addition, all numbers and expressions related to the quantities of components, reaction conditions, and the like used herein are to be understood as being modified by the term "about," unless otherwise indicated.

The terms first, second, and the like are used herein to describe various elements, and the elements should not be limited by the terms. The terms are used only for the purpose of distinguishing one element from another.

The integrated process for producing an aromatic compound and hydrogen according to an embodiment of the present invention comprises (1) coaromatizing a hydrocarbon feed comprising at least one of methane, ethane, and propane in the presence of a catalyst under the feeding of carbon dioxide to prepare an aromatic compound-containing product comprising at least one of benzene, toluene, and xylene, methane, hydrogen, and carbon monoxide; (2) separating from the aromatic compound-containing product (a) hydrogen, (b) the at least one of benzene, toluene, and xylene, and (c) a first methane-containing mixture comprising methane and carbon monoxide, respectively; and (3) subjecting the first methane-containing mixture to a water-gas shift to prepare a second methane-containing mixture comprising methane, hydrogen, and carbon dioxide.

Step (1)

In step (1), a hydrocarbon feed comprising at least one of methane, ethane, and propane is coaromatized in the presence of a catalyst under the feeding of carbon dioxide to prepare an aromatic compound-containing product comprising at least one of benzene, toluene, and xylene, methane, hydrogen, and carbon monoxide.

In a specific embodiment of the present invention, the hydrocarbon feed comprising at least one of methane, ethane, and propane may be shale gas, but it is not particularly limited thereto.

The hydrocarbon feed comprises at least one of methane, ethane, and propane, and it may further comprise other alkane or alkene components. The respective contents of methane, ethane, and propane in the hydrocarbon feed are not particularly limited, but the hydrocarbon feed may comprise 56 to 98% by mole of methane, 22% by mole or less of ethane, and 13% by mole or less of propane, based on the total number of moles of the hydrocarbon feed.

The hydrocarbon feed may further comprise a small amount of carbon dioxide ($CO_2$) and hydrogen sulfide ($H_2S$). The respective contents of carbon dioxide and hydrogen sulfide in the hydrocarbon feed are not particularly limited, but the hydrocarbon feed may contain 9.8% by mole or less of carbon dioxide and 0.4% by mole or less of hydrogen sulfide, based on the total number of moles of the hydrocarbon feed.

Since an acidic gas such as hydrogen sulfide contained in the hydrocarbon feed may deactivate the catalysts downstream in the process, it is desirable to remove it prior to coaromatizing the hydrocarbon feed. Thus, in a specific embodiment of the present invention, the integrated process for producing an aromatic compound and hydrogen may further comprise removing an acidic gas from the hydrocarbon feed.

The method for removing the acidic gas from the hydrocarbon feed is not particularly limited. For example, the acidic gas may be removed by contacting the hydrocarbon feed with an aqueous amine-based solution. Specifically, the acidic gas is removed by contacting the hydrocarbon feed with an aqueous solution of about 30% by weight of monoethanolamine (MEA) in an absorption tower. The aqueous MEA solution discharged from the absorption tower, which contains the acidic gas, may be recycled to the absorption tower once the acidic gas has been removed therefrom through, for example, distillation.

In addition, the hydrocarbon feed may contain a small amount of intermediate alkanes such as n-butane, i-butane, n-pentane, and i-pentane, along with nitrogen and water.

Meanwhile, the coaromatization reaction of light alkanes such as methane, ethane, and propane in the hydrocarbon feed may be represented by the following reaction schemes.

$6CH_4 \leftrightarrow C_6H_6 + 9H_2$ [Reaction Scheme 1]

$6C_2H_6 \leftrightarrow C_6H_6 + 2CH_4 + 5H_2$ [Reaction Scheme 2]

$3C_3H_8 \leftrightarrow C_6H_6 + 3CH_4 + 3H_2$ [Reaction Scheme 3]

$C_6H_6 + CH_4 \leftrightarrow C_7H_8 + H_2$ [Reaction Scheme 4]

As can be seen from the above reaction schemes, methane, ethane, and propane are each consumed through the coaromatization of light alkanes in the hydrocarbon feed, whereas a greater number of moles of methane than that consumed is produced through the cracking of ethane and propane.

The coaromatization reaction of light alkanes may be carried out in the presence of a catalyst. In a specific embodiment of the present invention, the catalyst for coaromatization of light alkanes may comprise a metal component selected from Ga, Zn, and Mo in an amount of 3 to 20% by weight, but it is not particularly limited thereto. In a preferred embodiment of the present invention, the catalyst for coaromatization of light alkanes may comprise Mo in an amount of about 10% by weight.

In addition, in a specific embodiment of the present invention, the catalyst for coaromatization of light alkanes may comprise a support selected from HZSM-5, ZSM-5, ZSM-11, ZSM-12, ZSM-23, and MCM-22, but it is not particularly limited thereto. Preferably, the catalyst for coaromatization of light alkanes may comprise an HZSM-5 support.

In a preferred embodiment of the present invention, the catalyst for coaromatization of light alkanes may be one in which an HZSM-5 support is impregnated with Mo in an amount of about 10% by weight.

When light alkanes are coaromatized in the presence of the catalyst, coke generated by pyrolyzing thermally less stable light alkanes rapidly deactivates the catalyst. Thus, it is necessary to regenerate the deactivated catalyst in order to continue the coaromatization reaction of light alkanes. Typically, the regeneration of the catalyst is carried out in a series of steps of lowering the temperature of the reactor after the reaction, regenerating the catalyst using oxygen in the air, and then heating it to the reaction temperature again for carburization (i.e., pretreatment).

The coaromatization reaction of light alkanes is carried out under the feeding of carbon dioxide. If carbon dioxide is supplied during the coaromatization of light alkanes, carbon dioxide reacts with light alkanes to cause dry reforming, which produces carbon monoxide and hydrogen in double moles. In addition, carbon dioxide may be adsorbed to the Mo-sites of the catalyst, thereby creating O* and C* or CO* (where * indicates a vacancy) and preventing coke from clogging Mo and the HZSM-5 support. Thus, if carbon dioxide is supplied during the coaromatization of light alkanes, the stability of the catalyst is enhanced, which extends the operation time of the reactor, and the generation of coke is suppressed, which reduces the cost for regenerating the catalyst.

The amount of carbon dioxide fed to the hydrocarbon feed may be 4.8 to 13.0% by volume based on the total volume of the hydrocarbon feed and carbon dioxide per hour. Preferably, the amount of carbon dioxide fed to the hydrocarbon feed may be 7.4 to 10.7% by volume based on the total volume of the hydrocarbon feed and carbon dioxide per hour. When the amount of carbon dioxide fed is within the above range, the activity of the catalyst can be maintained for a long period of time in a state in which the yield of the aromatic compounds is high.

In a specific embodiment of the present invention, the coaromatization reaction of light alkanes may be carried out in a multi-bed reactor having at least two reactors arranged in parallel. In a preferred embodiment of the present invention, the coaromatization reaction of light alkanes may be carried out in a multi-bed reactor having two reactors arranged in parallel. When the multi-bed reactor comprises two reactors, the coaromatization reaction of light alkanes may be carried out in one reactor, and the regeneration of the catalyst may be carried out in the other reactor. When the reaction and regeneration of the catalyst are completed in the respective reactors, the roles of the two reactors are then switched.

The reactors may each be a fixed bed or a fluidized bed equipped with the catalyst described above. In a specific embodiment of the present invention, the reactors may each comprise a fixed bed equipped with the above catalyst.

In a specific embodiment of the present invention, the coaromatization reaction of light alkanes may be carried out at a temperature of 700 to 800° C. and a pressure of 1 to 15 bar, and the reactor may be operated for 3 to 20 hours before the regeneration of the catalyst. In a preferred embodiment of the present invention, the coaromatization reaction of light alkanes may be carried out at a temperature of about 750° C. and a pressure of about 1 bar, and the reactor may be operated for 3 to 18 hours before the regeneration of the catalyst.

In addition, the regeneration of the catalyst may be carried out for 3 to 18 hours at a temperature of 500 to 550° C. and a pressure of about 1 bar. In a preferred embodiment of the present invention, the regeneration of the catalyst may be carried out for 3 to 16 hours at a temperature of about 500° C. and a pressure of about 1 bar. Here, the regeneration time of the catalyst may refer to the total time required for cooling after the reaction, regeneration of the catalyst using oxygen in the air, and carburization through temperature elevation.

In an embodiment of the present invention, the feeding of carbon dioxide during coaromatization of light alkanes enhances the stability of the catalyst, which extends the operation time of the reactor. Thus, the regeneration time of catalyst is sufficiently secured, which allows the amount of air supplied for the regeneration of the catalyst to be reduced, thereby enhancing the regeneration efficiency of the catalyst.

As a result of the coaromatization of light alkanes in the hydrocarbon feed, an aromatic compound-containing product comprising at least one of benzene, toluene, and xylene, methane, hydrogen, and carbon monoxide is produced. In a specific embodiment of the present invention, as a result of the coaromatization of light alkanes in the hydrocarbon feed, an aromatic compound-containing product comprising benzene, toluene, methane, hydrogen, and carbon monoxide may be produced.

In a specific embodiment of the present invention, the content of hydrogen in the aromatic compound-containing product as a product of the coaromatization of light alkanes in the hydrocarbon feed may be 17.3 to 36.0% by volume. In a preferred embodiment of the present invention, the content of hydrogen in the aromatic compound-containing product as a product of the coaromatization of light alkanes in the hydrocarbon feed may be about 26.4% by volume.

Step (2)

In step (2), (a) hydrogen, (b) the at least one of benzene, toluene, and xylene, and (c) a first methane-containing mixture comprising methane and carbon monoxide are separated from the aromatic compound-containing product, respectively.

Since the aromatic compound-containing product produced in step (1) above comprises aromatic compounds such as benzene, toluene, and xylene, methane, hydrogen, and carbon monoxide, it is necessary to separate them from each other.

First, hydrogen is separated from the aromatic compound-containing product. The method for separating hydrogen from the aromatic compound-containing product is not particularly limited, but it is preferable to use a membrane. The type of the membrane is not particularly limited as long as hydrogen can be separated from the aromatic compound-containing product, but a Matrimid® 5218 membrane may preferable be used. A Matrimid® 5218 membrane has a permeation rate of hydrogen and carbon monoxide of 2,394 and 43.89 GPUs, respectively. Its selectivity of hydrogen to carbon monoxide is 54.5. In addition, it has a selectivity of hydrogen to methane of 109.1. Thus, if it is used, high-purity hydrogen can be separated from the aromatic compound-containing product.

Subsequently, the aromatic compounds and the first methane-containing mixture comprising methane and carbon monoxide are separated from the aromatic compound-containing product from which hydrogen has been removed, respectively.

The method for separating the aromatic compounds and the first methane-containing mixture from the aromatic compound-containing product from which hydrogen has been removed is not particularly limited, but it is preferable to use distillation.

In a specific embodiment of the present invention, the separation of the aromatic compound-containing product from which hydrogen has been removed may be carried out through distillation using at least two columns.

When the separation of the aromatic aromatic-containing product from which hydrogen has been removed is carried out through distillation using two columns, the first methane-containing mixture and the aromatic compounds such as benzene, toluene, and/or xylene are separated in the first column. As a result, the first methane-containing mixture comprising methane and carbon monoxide as main components and a small amount of ethane, ethylene, and the like is obtained as an overhead stream. A mixture comprising benzene and toluene is obtained as a bottom stream. The overhead stream is to be used in a water-gas shift (WGS) reaction for the production of hydrogen, and the bottoms stream is fed to a second column for further separation.

The mixture comprising benzene and toluene is separated in the second column, so that a product mainly comprising benzene is obtained as an overhead stream, and a product mainly comprising toluene is obtained as a bottom stream. Benzene and toluene thus obtained may be stored, respectively.

The type of the distillation columns is not particularly limited, but a sieve tray type is preferable.

The operating conditions of the distillation columns are not particularly limited as long as the first methane-containing mixture and the aromatic compounds and the respective aromatic compounds can be separated. Preferably, the first column is operated at a high pressure (e.g., 20-40 bar, preferably about 30 bar), and the second column is operated at a low pressure (e.g., 1-5 bar, preferably about 1 bar).
Step (3)

In step (3), the first methane-containing mixture is subjected to a water-gas shift to prepare a second methane-containing mixture comprising methane, hydrogen, and carbon dioxide.

In order to produce hydrogen from the first methane-containing mixture, in an embodiment of the present invention, the first methane-containing mixture may be subjected to a water-gas shift.

The water-gas shift reaction may be represented by the following Reaction Scheme 5.

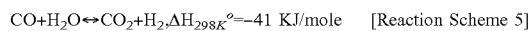

$CO + H_2O \leftrightarrow CO_2 + H_2, \Delta H_{298K}^{\circ} = -41$ KJ/mole [Reaction Scheme 5]

As can be seen from Reaction Scheme 5, carbon monoxide in the first methane-containing mixture mainly comprising methane and carbon monoxide is converted to carbon dioxide and hydrogen through the water-gas shift reaction; thus, a second methane-containing mixture comprising methane, hydrogen, and carbon dioxide is produced as a result of the water-gas shift reaction.

The water-gas shift reaction may be carried out in the presence of a catalyst. Examples of the catalyst used in the water-gas shift reaction may include metal catalysts such as Cu/Zn, Cu/Zn/Al, and Fe/Cr. In a specific embodiment of the present invention, the water-gas shift reaction may be carried out in the presence of a Pt/ZrO$_2$ catalyst, but it is not particularly limited thereto.

In a specific embodiment of the present invention, the water-gas shift reaction may be carried out, for example, at a temperature of about 300° C. and a pressure of about 30 bar.

In a specific embodiment of the present invention, the content of hydrogen in the second methane-containing mixture, which is a product of the water-gas shift reaction, may be 24 to 55% by volume. In a preferred embodiment of the present invention, the content of hydrogen in the second methane-containing mixture as a product of the water-gas shift reaction may be about 38.4% by volume.

The integrated process for producing an aromatic compound and hydrogen according to an embodiment of the present invention may further comprise separating hydrogen from the second methane-containing mixture.

The method for separating hydrogen from the second methane-containing mixture is not particularly limited, but it is preferable to use a membrane. The type of the membrane is not particularly limited as long as hydrogen can be separated from the second methane-containing mixture, but a Matrimid® 5218 membrane may preferably be used. If a Matrimid® 5218 membrane is used, high-purity hydrogen can be separated from the second methane-containing mixture.

Subsequently, the integrated process for producing an aromatic compound and hydrogen according to an embodiment of the present invention may further comprise separating the second methane-containing mixture from which hydrogen has been removed to a hydrocarbon mixture comprising methane as a main component and further comprising ethane, ethylene, and the like and residual components comprising carbon dioxide, carbon monoxide, and water, respectively.

The method for separating the residual components from the second methane-containing mixture from which hydrogen has been removed is not particularly limited. For example, a commercially available carbon capture and storage process may be used. In such an event, the carbon capture and storage process may be substantially the same as the process for removing acidic gases from the hydrocarbon feed in step (1).

Specifically, the second methane-containing mixture from which hydrogen has been removed is contacted with an aqueous solution of about 30% by weight of monoethanolamine (MEA) in an absorption tower to remove the residual components such as carbon dioxide and carbon monoxide. The aqueous MEA solution discharged from the absorption tower, which contains the residual components, may be recycled to the absorption tower once the residual components have been removed therefrom through, for example, distillation.

Since the hydrocarbon mixture from which the residual components have been removed comprises methane as a main component and further comprises ethane and ethylene, it may be used for the production of synthesis gas. The residual components comprising carbon dioxide, carbon monoxide, and water may be recycled to the coaromatization of light alkanes or may be discarded once water has been removed. In the former case, some of the recycled residual components must be purged to prevent the build-up of impurities in the entire process.

Example

Hereinafter, the present invention will be described in more detail with reference to examples. However, the examples are intended to describe the present invention in more detail, and the scope of the present invention is not limited by these examples.

Referring to FIG. 1, the integrated process for producing an aromatic compound and hydrogen according to an embodiment of the present invention is, for example, carried out using a shale gas treatment unit (100), a BTX production unit (200), a BTX separation unit (300), and a water-gas shift unit (400).

The data of the integrated process for producing an aromatic compound and hydrogen according to an embodiment of the present invention were basically obtained through process simulation using Aspen Plus™.

Shale Gas Treatment Unit (100)

The shale gas treatment unit (100) is a unit for removing an acidic gas such as hydrogen sulfide (H$_2$S) contained in shale gas (110) as a raw material. The composition and supply conditions of the shale gas (110) feed are shown in Table 1 below, and its feed rate is set to 100 MT/hr.

TABLE 1

| Composition (% by mole) | $CH_4$ | 80 |
|---|---|---|
| | $C_2H_6$ | 10 |
| | $C_3H_8$ | 5 |
| | $CO_2$ | 4.9 |
| | $H_2S$ | 0.1 |
| Temperature (° C.) | | 40 |
| Pressure (bar) | | 1 |

The shale gas (110) feed is pressurized through a compressor (120), and the pressurized shale gas (121) is supplied to the bottom of a column (130). Specifically, the column (130) is an absorption tower provided with structured packings therein. The shale gas (121) supplied to the bottom of the column (130) is in countercurrent contact with an aqueous solution of about 30% by weight of monoethanolamine (MEA) flowing down from the top of the column (130). As a result, the shale gas from which the acidic gases have been removed is discharged from the top of the column (130), and the aqueous MEA solution containing the acidic gases is discharged from the bottom of the column (130).

The shale gas (131) discharged from the top of the column (130) is introduced into a flash drum (140). In the flash drum (140), water and MEA are separated from the shale gas and recycled (141) to the column (130), and the shale gas (142) discharged from the flash drum (140) is introduced into a dehydrator (150). The dehydrator (150) is an apparatus for removing water using calcium chloride, zeolite, or the like. The shale gas (152) from which water (151) has been removed in the dehydrator (150) is supplied to a BTX production unit (200).

Meanwhile, the aqueous MEA solution (132) discharged from the column (130) is introduced into a heat exchanger (160) through a pump (135). The aqueous MEA solution (161) discharged from the heat exchanger (160) is supplied to a column (170). The column (170) is a distillation tower provided with random packings therein. The aqueous MEA solution and the acidic gases (e.g., $CO_2$ and $H_2S$) are separated from each other in the column (170).

The acidic gases separated from the aqueous MEA solution are discharged from the top of the column (170). The aqueous MEA solution from which the acidic gases have been removed is discharged from the bottom of the column (170). The acidic gases (171) discharged from the top of the column (170) are introduced into a flash drum (180). In the flash drum (180), water and MEA are separated from the acidic gases and recycled (181) to the column (170), and the acidic gases (182) discharged from the flash drum (180) are stored.

The aqueous MEA solution (172) discharged from the bottom of the column (170) is introduced into the heat exchanger (160). The aqueous MEA solution (162) discharged from the heat exchanger (160) is introduced to a cooler (190). The aqueous MEA solution (191) cooled in the cooler (190) is supplied to the top of the column (130) and used again to remove acidic gases from shale gas.

The operating conditions of the respective apparatuses in the shale gas treatment unit (100) are shown in Table 2 below. In addition, the material balance of the inlet and outlet streams of the shale gas treatment unit (100) is shown in Table 3 below (hereinafter, the flow rate of each stream of each unit is in kg/hr).

TABLE 2

| | Ref. numeral | | | |
|---|---|---|---|---|
| | 120 | 130 | 135 | 140 |
| Apparatus | Compressor | Column | Pump | Flash drum |
| Type | Centrifugal | Structured packings | — | — |
| Temp. (° C.) | — | — | — | 40 |
| Pressure (bar) | 1.12 | 1 | 3 | 1 |
| Ref. numeral | 160 | 170 | 180 | 190 |
| Apparatus | Heat exchanger | Column | Flash drum | Cooler |
| Type | Shell-tube | Random packings | — | Shell-tube |
| Temp. (° C.) | 5$^a$ | 123$^b$ | 40 | 40 |
| Pressure (bar) | 3 | 2 | 2 | 1.5 |

$^a$indicates a temperature difference between the shale gas (162) and the shale gas (132).
$^b$indicates the temperature of the reboiler.

TABLE 3

| | Ref. numeral | | | |
|---|---|---|---|---|
| | 110 | 151 | 152 | 182 |
| $CH_4$ | 63,283.3 | — | 63,274.5 | 8.8 |
| $C_2H_6$ | 14,826.8 | — | 14,824.5 | 2.3 |
| $C_3H_8$ | 10,871.6 | — | 10,870.3 | 1.3 |
| $C_2H_4$ | — | — | — | — |
| $H_2$ | — | — | — | — |
| CO | — | — | — | — |
| $C_6H_6$ | — | — | — | — |
| $C_7H_8$ | — | — | — | — |
| $H_2O$ | — | 6,408.48 | — | 170.8 |
| $CO_2$ | 10,850.2 | 130.0 | — | 10,720.2 |
| $H_2S$ | 168.0 | — | — | 168.0 |
| $O_2$ | — | — | — | — |

BTX Production Unit (200)

The shale gas (152) discharged from the shale gas treatment unit (100) is introduced into a reactor (220a or 220b) once carbon dioxide (210) has been supplied thereto. Here, carbon dioxide may also be directly supplied to the reactor (220a or 220b). Light alkane components such as methane, ethane, and propane are coaromatized in the reactor (220a or 220b) to produce an aromatic compound-containing product (221) comprising benzene and toluene, along with methane, hydrogen, and carbon monoxide. This aromatic compound-containing product (221) is introduced into a compressor (310).

The operating conditions of the respective apparatuses in the BTX production unit (200) are shown in Table 4 below. In addition, the material balance of the inlet and outlet streams of the BTX production unit (200) is shown in Table 5 below.

TABLE 4

| | Ref. numeral | | |
|---|---|---|---|
| | 220a | 220b | 310 |
| Apparatus | Reactor | Reactor | Compressor |
| Type | Fixed bed | Fixed bed | Centrifugal |
| Temp. (° C.) | 750 | 750 | — |
| Pressure (bar) | 1 | 1 | 30 |

TABLE 5

| | Ref. numeral | | |
|---|---|---|---|
| | 152 | 210 | 221 |
| $CH_4$ | 63,274.5 | — | 73,733.0 |
| $C_2H_6$ | 14,824.5 | — | 111.0 |
| $C_3H_8$ | 10,870.3 | — | — |
| $C_2H_4$ | — | — | 247.6 |
| $H_2$ | — | — | 3,634.9 |
| CO | — | — | 25,737.6 |
| $C_6H_6$ | — | — | 6,939.8 |
| $C_7H_8$ | — | — | 262.3 |
| $H_2O$ | — | — | — |
| $CO_2$ | — | 21,697.0 | — |
| $H_2S$ | — | — | — |
| $O_2$ | — | — | — |

Meanwhile, in order to quantify the effect of carbon dioxide supplied to shale gas, an experiment was conducted using a catalyst impregnated with Mo in an amount of about 10% by weight on an HZSM-5 support. The catalyst was prepared by impregnating ammonium molybdate tetrahydrate (($NH_4$)$_6$$Mo_7$$O_{24}$-$4H_2O$) on a commercially available HZSM-5 support (Zeolite ZSM-5 from Alfa Aesar, ammonium, Powder, SA 425 m/g, $SiO_2$:$Al_2O_3$ molar ratio 23:1) using the wetness impregnation method.

A laboratory-scale fixed bed reactor was prepared, and about 0.2 g of the catalyst was used. The reactor was operated at atmospheric pressure, and the total gas hourly space velocity (GHSV) during the reaction was fixed at 3 L/g cat.-hr. The amount of carbon dioxide supplied to shale gas was changed as shown in Table 6 below. The results are shown in FIGS. 2 to 6.

Figure 7:
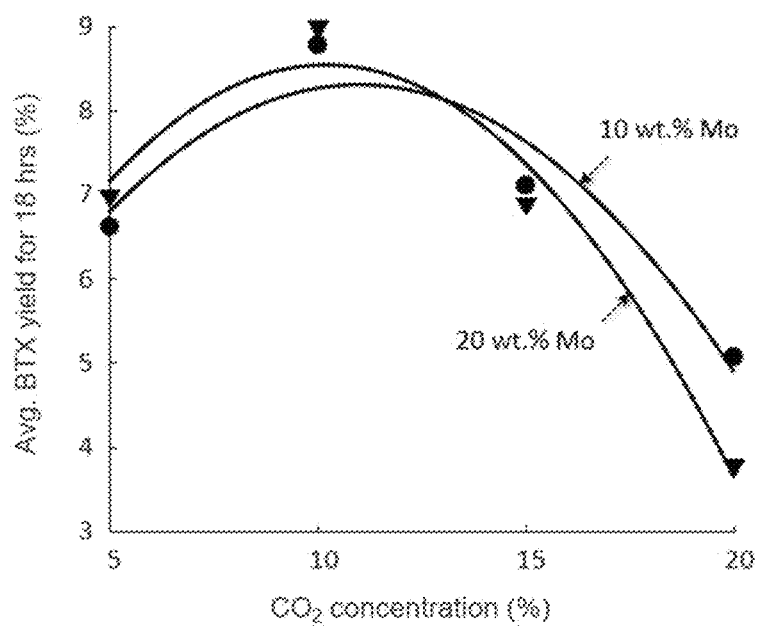
FIG. 7 is a graph showing the average yield of BTX with respect to the feed rate of carbon dioxide according to the loading amount of Mo.

In addition, an additional experiment was conducted using a catalyst impregnated with Mo in an amount of about 20% by weight on the HZSM-5 support. The results are shown in FIG. 7.

TABLE 6

| | Test Example | | | | |
|---|---|---|---|---|---|
| | 1 | 2 | 3 | 4 | 5 |
| Total gas flow rate (L/g cat.-hr) | | | 3.0 | | |
| Shale gas flow rate (L/g cat.-hr) | | | 1.5 | | |
| Balance gas flow rate (L/g cat.-hr)[a] | | | 1.5 | | |
| $N_2$ concentration in the balance gas (vol. %) | 100 | 95 | 90 | 85 | 80 |
| $CO_2$ concentration in the balance gas (vol. %) | 0 | 5 | 10 | 15 | 20 |
| Temp. (° C.) | | | 750 | | |

[a]The balance gas is a mixed gas of nitrogen and carbon dioxide.

Figure 2:
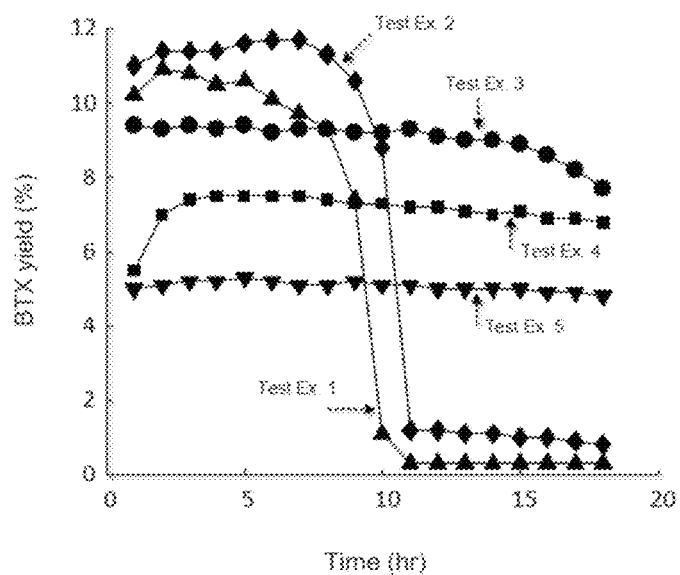
FIG. 2 is a graph showing the BTX yield with respect to time according to the feed rate of carbon dioxide.

FIG. 2 is a graph showing the BTX yield with respect to time according to the feed rate of carbon dioxide. When carbon dioxide was not supplied (Test Example 1), the BTX yield converged to 0% after 10 hours of reaction, which seems to be attributable to the deactivation of the catalyst by coke. On the other hand, when about 9.1% by volume of carbon dioxide was supplied (Test Example 3), it was confirmed that the BTX yield was maintained at about 8% even up to 18 hours of reaction.

Figure 3:
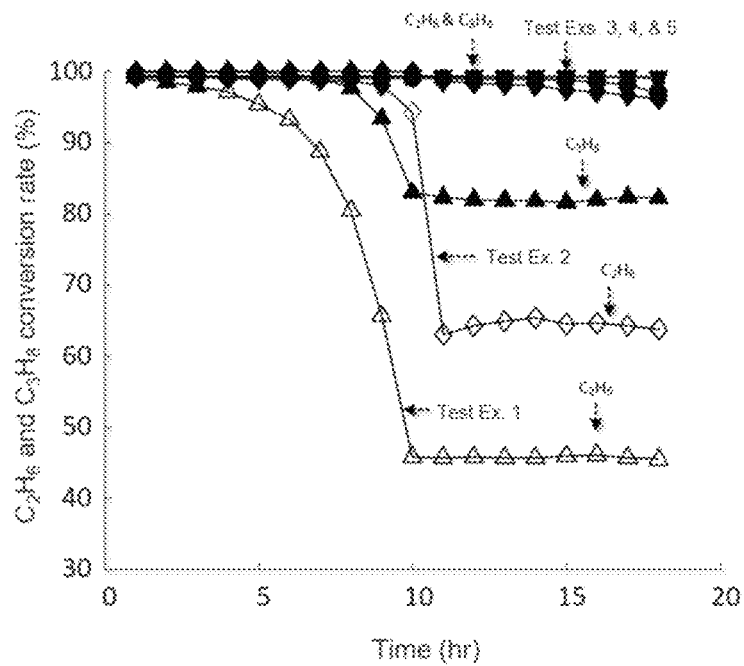
FIG. 3 is a graph showing the conversion rate of ethane and propane with respect to time according to the feed rate of carbon dioxide.

FIG. 3 is a graph showing the conversion rate of ethane and propane with respect to time according to the feed rate of carbon dioxide. In Test Example 1, the conversion rate of ethane and propane was rapidly reduced due to the deactivation of the catalyst after 10 hours of reaction. On the other hand, in Test Example 3, it was confirmed that the conversion rate of ethane and propane was maintained at about 95% even up to 18 hours of reaction.

Figure 4:
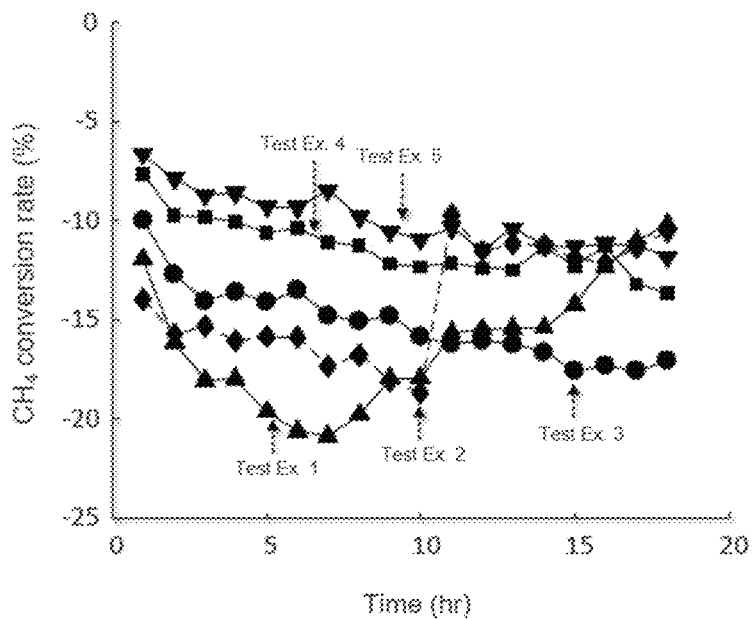
FIG. 4 is a graph showing the conversion rate of methane with respect to time according to the feed rate of carbon dioxide.

FIG. 4 is a graph showing the conversion rate of methane with respect to time according to the feed rate of carbon dioxide. In Test Example 1, the amount of methane produced from ethane and propane increased until 7 hours of reaction, so that the conversion rate of methane was decreased. Thereafter, the amount of methane produced from ethane and propane decreased due to the deactivation of the catalyst, so that the conversion rate of methane appeared to have increased. On the other hand, in Test Example 3, the activity of the catalyst was maintained until 18 hours of reaction, indicating a trend that the conversion rate of methane gradually decreased.

Figure 5:
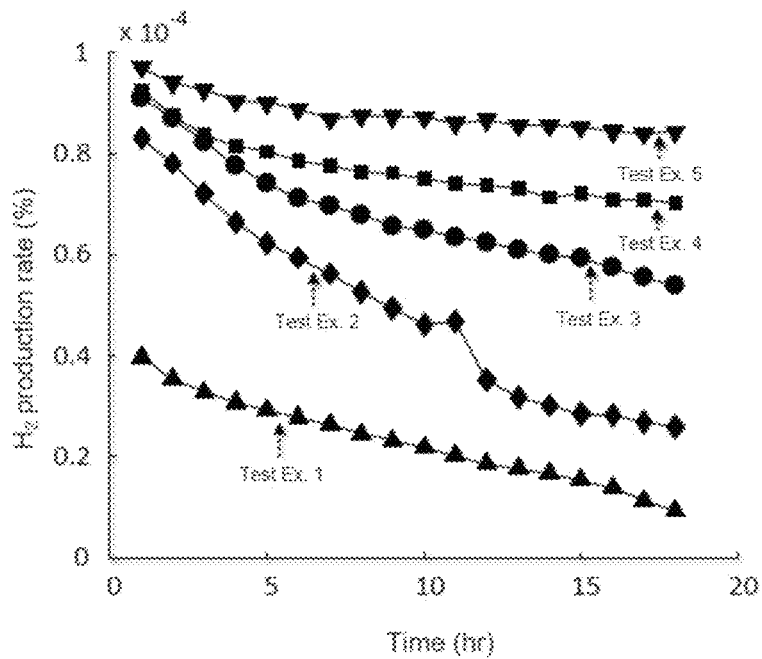
FIG. 5 is a graph showing the production rate of hydrogen with respect to time according to the feed rate of carbon dioxide.

FIG. 5 is a graph showing the production rate of hydrogen with respect to time according to the feed rate of carbon dioxide. In Test Example 3, the production rate of hydrogen was maintained higher than that in Test Example 1.

Figure 6:
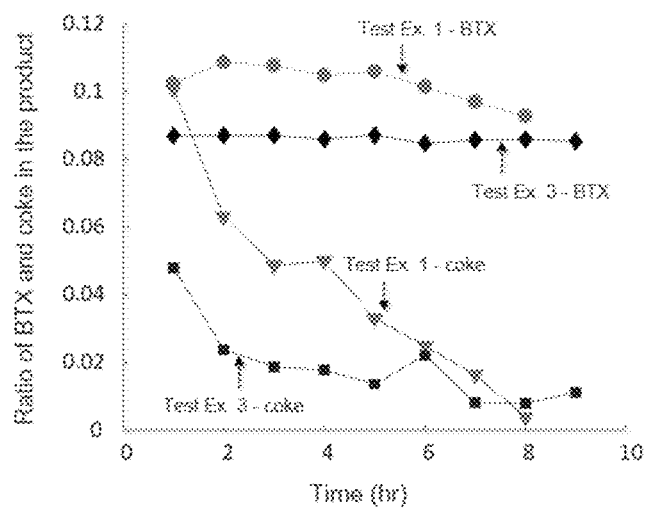
FIG. 6 is a graph showing the production rates of BTX and coke with respect to time according to the feed rate of carbon dioxide.

FIG. 6 is a graph showing the production rates of BTX and coke with respect to time according to the feed rate of carbon dioxide. In Test Example 1, since the catalyst was deactivated over time, the production rates of both BTX and coke decreased. On the other hand, in Test Example 3, since the deactivation of the catalyst over time was small, the decrease in the production rates of BTX and coke was relatively small. In addition, the production rate of coke in Test Example 3 was smaller than that in Test Example 1.

FIG. 7 is a graph showing the average yield of BTX with respect to the feed rate of carbon dioxide according to the amount of Mo impregnated. When the amount of carbon dioxide supplied to shale gas was in the range of 4.8 to 13.0% by volume, the yield of BTX was maintained high. Here, it can be seen that the yield of BTX is not significantly affected by the amount of Mo impregnated in the catalyst.

BTX Separation Unit (300)

The aromatic compound-containing product (221) discharged from the BTX production unit (200) is pressurized through a compressor (310). The pressurized aromatic compound-containing product (311) passes through a membrane (320) to separate hydrogen (321). Subsequently, the aromatic compound-containing product (322) from which hydrogen has been removed is supplied to a first column (330). The first column (330) is a distillation tower provided with sieve trays therein. In the first column (330), a mixture comprising benzene and toluene is obtained as a bottom stream (331), and a first methane-containing mixture comprising methane and carbon monoxide as main components and a small amount of ethane, ethylene, and the like is obtained as an overhead stream (332).

The bottom stream (331) of the first column (330) is fed to the second column (340). The second column (340) is a distillation tower provided with sieve trays therein. In the second column (340), a product mainly comprising benzene is obtained as an overhead stream (341), and a product mainly comprising toluene is obtained as a bottom stream (342). Benzene and toluene thus obtained are stored, respectively.

Meanwhile, the first methane-containing mixture as an overhead stream (332) of the first column (330) is supplied to a water-gas shift unit (400).

The operating conditions of the respective apparatuses in the BTX separation unit (300) are shown in Table 7 below. In addition, the material balance of the inlet and outlet streams of the BTX separation unit (300) is shown in Table 8 below.

TABLE 7

| | Ref. numeral | | |
|---|---|---|---|
| | 320 | 330 | 340 |
| Apparatus Type | Membrane Matrimid ® 5218[a] | Column Sieve trays | Column Sieve trays |
| Temp. (° C.) | 40-300 | — | — |
| Pressure (bar) | 30 | 30 | 1 |

[a] module porosity 0.36, hollow fiber outer diameter 0.3 mm, and hollow fiber inner diameter 0.2 mm

TABLE 8

| | Ref. numeral | | | | |
|---|---|---|---|---|---|
| | 221 | 321 | 332 | 341 | 342 |
| $CH_4$ | 73,733.0 | — | 73,733.0 | — | — |
| $C_2H_6$ | 111.0 | — | 111.0 | — | — |
| $C_3H_8$ | — | — | — | — | — |
| $C_2H_4$ | 247.6 | — | 247.6 | — | — |
| $H_2$ | 3,634.9 | 3,634.9 | — | — | — |
| CO | 25,737.6 | — | 25,737.6 | — | — |
| $C_6H_6$ | 6,939.8 | — | — | 6,939.8 | — |
| $C_7H_8$ | 262.3 | — | — | — | 262.3 |
| $H_2O$ | — | — | — | — | — |
| $CO_2$ | — | — | — | — | — |
| $H_2S$ | — | — | — | — | — |
| $O_2$ | — | — | — | — | — |

Water-Gas Shift Unit (400)

The overhead stream (332) of the first column (330) in the BTX separation unit (300) is fed to a reactor (410). In the reactor (410), a water-gas shift reaction is carried out in which carbon monoxide reacts with water in the presence of a $Pt/ZrO_2$ catalyst to be converted to carbon dioxide and hydrogen.

The second methane-containing mixture (411) comprising hydrogen passes through a membrane (420) to separate hydrogen (421). Subsequently, the second methane-containing mixture (422) from which hydrogen has been removed is introduced to a carbon capture and storage (CCS) apparatus (430). Since the hydrocarbon mixture separated in the CCS (430) comprises methane as a main component and further comprises ethane and ethylene, it is discharged for further use. Meanwhile, the residual components (432) separated from the CCS (430) comprise carbon dioxide, carbon monoxide, and water. It is discharged for recycling once water has been removed or discarded.

The operating conditions of the respective apparatuses in the water-gas shift unit (400) are shown in Table 9 below. In addition, the material balance of the inlet and outlet streams of the water-gas shift unit (400) is shown in Table 10 below.

TABLE 9

| | Ref. numeral | | |
|---|---|---|---|
| | 410 | 420 | 430 |
| Apparatus Type | Reactor | Membrane Matrimid ® 5218[a] | CCS Using MEA |
| Temp. (° C.) | 300 | 40-300 | — |
| Pressure (bar) | 1 | 1 | — | a: module porosity 0.36, hollow fiber outer diameter 0.3 mm, and hollow fiber inner diameter 0.2 mm

TABLE 10

| | Ref. numeral | | | |
|---|---|---|---|---|
| | 332 | 421 | 431 | 432 |
| $CH_4$ | 73,733.0 | — | 73,733.0 | — |
| $C_2H_6$ | 111.0 | — | 111.0 | — |
| $C_3H_8$ | — | — | — | — |
| $C_2H_4$ | 247.6 | — | 247.6 | — |
| $H_2$ | — | 1,828.6 | — | — |
| CO | 25,737.6 | — | — | 329.3 |
| $C_6H_6$ | — | — | — | — |
| $C_7H_8$ | — | — | — | — |
| $H_2O$ | — | — | — | 5,616.4 |
| $CO_2$ | — | — | — | 39,921.4 |
| $H_2S$ | — | — | — | — |
| $O_2$ | — | — | — | — |

As can be seen from the above example, the integrated process for producing an aromatic compound and hydrogen according to an embodiment of the present invention can efficiently and continuously produce high value-added aromatic compounds and hydrogen without the need to separate methane from shale gas through, e.g., cryogenic distillation.

In addition, the integrated process for producing an aromatic compound and hydrogen according to an embodiment of the present invention can increase the regeneration efficiency of the catalyst and reduce the regeneration cost while extending the operating time of the reactor for producing aromatic compounds from shale gas.

What is claimed is:

1. An integrated process for producing an aromatic compound and hydrogen, which comprises:
   (1) coaromatizing a hydrocarbon feed comprising at least one of methane, ethane, and propane in the presence of a catalyst while feeding carbon dioxide to the hydrocarbon feed or to a reactor in which the coaromatization reaction is carried out to prepare an aromatic compound-containing product comprising at least one of benzene, toluene, and xylene, methane, hydrogen, and carbon monoxide;
   (2) separating from the aromatic compound-containing product (a) hydrogen, (b) the at least one of benzene, toluene, and xylene, and (c) a first methane-containing mixture comprising methane and carbon monoxide, respectively; and
   (3) subjecting the carbon monoxide of the first methane-containing mixture to a water-gas shift reaction to prepare a second methane-containing mixture comprising methane, hydrogen, and carbon dioxide.

2. The integrated process for producing an aromatic compound and hydrogen of claim 1, wherein the hydrocarbon feed is shale gas.

3. The integrated process for producing an aromatic compound and hydrogen of claim 1, wherein the hydrocarbon feed comprises 56 to 98% by mole of methane.

4. The integrated process for producing an aromatic compound and hydrogen of claim 1, which further comprises removing an acidic gas from the hydrocarbon feed before step (1).

5. The integrated process for producing an aromatic compound and hydrogen of claim 1, wherein the catalyst in step (1) comprises a metal component selected from Ga, Zn, and Mo in an amount of 3 to 20% by weight.

6. The integrated process for producing an aromatic compound and hydrogen of claim 5, wherein the catalyst in step (1) comprises Mo.

7. The integrated process for producing an aromatic compound and hydrogen of claim 1, wherein the catalyst in step (1) comprises a support selected from HZSM-5, ZSM-5, ZSM-11, ZSM-12, ZSM-23, and MCM-22.

8. The integrated process for producing an aromatic compound and hydrogen of claim 7, wherein the catalyst in step (1) comprises a HZSM-5 support.

9. The integrated process for producing an aromatic compound and hydrogen of claim 1, wherein the catalyst in step (1) is one in which an HZSM-5 support is impregnated with Mo in an amount of 10% by weight.

10. The integrated process for producing an aromatic compound and hydrogen of claim 1, wherein the coaromatization reaction of the hydrocarbon feed in step (1) is carried out in a multi-bed reactor having at least two reactors arranged in parallel.

11. The integrated process for producing an aromatic compound and hydrogen of claim 10, wherein the reactors each comprise a fixed bed equipped with the catalyst.

12. The integrated process for producing an aromatic compound and hydrogen of claim 1, wherein, in step (1), the coaromatization reaction of the hydrocarbon feed is carried out at a temperature of 700 to 800° C. and a pressure of 1 to 15 bar, the reactor is operated for 3 to 20 hours before the regeneration of the catalyst, and the regeneration of the catalyst is carried out for 3 to 18 hours at a temperature of 500 to 550° C. and a pressure of 1 bar.

13. The integrated process for producing an aromatic compound and hydrogen of claim 1, wherein the content of hydrogen in the aromatic compound-containing product is 17.3 to 36.0% by volume.

14. The integrated process for producing an aromatic compound and hydrogen of claim 1, which comprises separating hydrogen from the aromatic compound-containing product in step (2), wherein the separation of hydrogen from the aromatic compound-containing product is carried out using a membrane.

15. The integrated process for producing an aromatic compound and hydrogen of claim 14, which comprises separating a first methane-containing mixture comprising methane and carbon monoxide from the aromatic compound-containing product from which hydrogen has been removed, wherein the separation of the first methane-containing mixture comprising methane and carbon monoxide from the aromatic compound-containing product from which hydrogen has been removed is carried out through distillation using at least two columns.

16. The integrated process for producing an aromatic compound and hydrogen of claim 1, wherein the content of hydrogen in the second methane-containing mixture is 24 to 55% by volume.

17. The integrated process for producing an aromatic compound and hydrogen of claim 1, which further comprises separating hydrogen from the second methane-containing mixture obtained in step (3), wherein the separation of hydrogen from the second methane-containing mixture is carried out using a membrane.

18. The integrated process for producing an aromatic compound and hydrogen of claim 17, which further comprises separating the second methane-containing mixture from which hydrogen has been removed in step (3) to a hydrocarbon mixture comprising methane, ethane, and ethylene and residual components comprising carbon dioxide, carbon monoxide, and water, respectively, wherein the separation of the second methane-containing mixture from which hydrogen has been removed to the hydrocarbon mixture and the residual components is carried out using a carbon capture and storage process.

\* \* \* \* \*